United States Patent [19]

Fleischhackor et al.

[11] Patent Number: 5,395,329
[45] Date of Patent: Mar. 7, 1995

[54] CONTROL HANDLE FOR STEERABLE CATHETER

[75] Inventors: John J. Fleischhacker; John D. Ockuly; Laurel A. Kurth, all of Minnetonka, Minn.

[73] Assignee: Daig Corporation, Minnetonka, Minn.

[21] Appl. No.: 183,655

[22] Filed: Jan. 19, 1994

[51] Int. Cl.⁶ .............................................. A61M 37/00
[52] U.S. Cl. ......................................... 604/95; 604/280
[58] Field of Search ................. 604/95, 164, 165, 167, 604/281, 282, 280; 128/657, 698, 772

[56] References Cited

U.S. PATENT DOCUMENTS

| | | | |
|---|---|---|---|
| 5,185,004 | 2/1993 | Lashinski | 604/95 |
| 5,195,968 | 3/1993 | Lundquist et al. | 604/95 |
| 5,273,535 | 12/1993 | Edwards et al. | 604/95 |
| 5,275,151 | 1/1994 | Shockey et al. | 128/772 X |

*Primary Examiner*—John D. Yasko
*Attorney, Agent, or Firm*—Scott R. Cox

[57] ABSTRACT

A steerable catheter comprised of an elongated catheter body containing one or more lumen; a catheter tip fixedly secured to the distal end of the catheter body and a steerable catheter handle attached to the proximal end of the catheter body wherein said steerable catheter handle is comprised of a mounting shaft containing a geared slide, a slide block, a slide block adjustment screw, and an adjustment screw guide; an adjustment knob comprised of a geared inset and an external rotation element for rotating the adjustment knob, a handle grip which fits over the mounting shaft and electrical connectors for attachment to the proximal end of the mounting shaft and which contain electrode electrical wires.

31 Claims, 7 Drawing Sheets

CONTROL HANDLE FOR STEERABLE CATHETER

BACKGROUND OF INVENTION

1. Field of Invention

This invention relates to steerable catheters. More particularly, this invention relates to an improved control handle for a steerable catheter which precisely and consistently controls the deflection of the tip of the catheter.

2. Prior Art

Catheters of various types have been utilized for medical procedures for many years. For example, they have been used to convey an electric stimulus to a selected location within the human body or to monitor or make measurements for diagnostic purposes of activities within the human body. Such catheters examine, diagnose and treat areas which are otherwise unaccessible without invasive procedures. In use, the catheter is first inserted into a major vein or artery or other body lumen which is near the body surface. The catheter is then guided to the area for examination, diagnosis or treatment by manipulating the catheter through the body lumen. As the utilization of catheters in remote and difficult to reach locations within the body has increased, it has become more important to control precisely the movement of the tip of the catheter within the body lumen.

Control of the movement of catheters is difficult because of their construction. The body of conventional catheters is long and tubular. To provide sufficient control over the movement of the catheter, it is necessary that these tubular catheters be made somewhat rigid. However, catheters must be flexible enough to navigate through the body lumen to arrive at the desired location within the body where the medical procedures will be performed without harming the body lumen.

One of the early methods used to control the movement of catheters within a body was by the use of pre-shaped catheter tips. This construction had advantages for certain limited medical procedures but because the configuration of the bend could not be changed after insertion and because of the difficulty in orienting the bend in the desired direction as a result of the torsional flexibility of the catheter, new improved catheters were necessary.

Short and rigid controllable tip devices have also been used for special procedures where the degree of bending of the tip could be controlled from the handle. However, these devices are not satisfactory for vascular purposes where the catheter must be long, slender and flexible throughout its entire length.

To increase the ability to move and navigate within a body, longer, flexible catheters containing steerable, deflectable tips have been designed. Because the deflectable tips of these flexible catheters are bendable, they can be used for a number of medical procedures which require precise control over the orientation of the catheter tip. With these devices the deflection of the steerable tip is achieved by increasing or decreasing the axial compressive force on one side of the steerable tip by applying tension to the pull wire. By increasing the compressive force to one side of the tip, it is deflected in a predetermined direction.

To control precisely the movement of these steerable catheters, control handles have been attached at the proximal end of the catheter body. For example, U.S. Pat. No. 4,586,923 describes certain devices useful for controlling the movement of steerable catheters.

Various other types of control handles have been designed to control the movement of steerable catheters. For example, U.S. Pat. No. 5,195,968 discloses a design for a catheter steering mechanism which is designed to bend the tip of a catheter. See also U.S. Pat. No. 5,254,088, a related application. U.S. Pat. No. 5,185,004 also discloses a steerable catheter handle for use with a steerable catheter system.

Another control handle which can be rotated while in use is disclosed in U.S. Pat. No. 4,960,134. This patent discloses a rotatable catheter handle which uses a piston contained within the control handle to create and maintain pressure on the pull wire. As the piston is extended from the control handle, the catheter tip is bent. See also, U.S. Pat. Nos. 5,125,896, 4,874,371 and 5,002,560.

Other medical procedures also use medical instruments containing guidewires with bendable tips and control handles. See for example, U.S. Pat. Nos. 5,035,696, 4,799,496, and 3,521,620. While each of these devices uses a handle to control the deflection of the tip, precise one-handed control of the movement and deflection of the catheter tip is still a problem. In addition, precise control of the movement of the catheter tip even when the handle is being rotated must still be maintained.

Medical procedures utilizing these steerable catheters frequently require an extended period of time to complete by even skilled medical practitioners. Such procedures lasting many hours create problems of control of the catheter tip even with existing steerable catheter handles. Further, as most of these procedures are done with only a single hand of the physician controlling the movement of the catheter, it is important to provide a mechanism to limit the movement of the tip while maintaining the tip in an existing bent position. Thus, a new handle which precisely controls the movement of the catheter tip and which is easy to use is still needed.

Accordingly, it is an object of this invention to disclose a steerable catheter with an improved control handle.

Another object of this invention is to disclose a steerable catheter with an adjustable control handle which has precise control of the deflection of the tip of the catheter.

Another object of this invention is to disclose a steerable catheter with control handle wherein the control handle can be operated by use of only one hand of the medical practitioner.

Another object of this invention is to disclose a steerable catheter which operates in the same manner regardless of its rotational orientation.

It is a still further object of this invention to disclose a steerable catheter with a control handle wherein the deflection of the tip can be maintained in a set position during use.

These and other objects are obtained by the design of the control handle of the steerable catheter of the instant invention.

SUMMARY OF INVENTION

The instant invention comprises a steerable catheter handle for steerable catheters composed of a handle grip, a mounting shaft, an adjusting knob, the proximal end of a pull wire and an electrical connector containing electrode electrical wires useful for performing the required medical procedures. The mounting shaft of the control handle contains a geared slide, a slide block, an adjustment screw guide, a spacer block and a slide block adjustment screw. The internally threaded adjusting knob, when turned axially, propels the geared slide which holds the slide block, either forward or backward. The pull wire which is secured to the slide block and is thus pulled backward as the geared slide moves forward or backward within the mounting shaft. As the pull wire is pulled backward, the distal tip of the catheter is deflected. The electrical wires for diagnosis, testing and performing medical procedures pass through the adjusting knob, mounting shaft and handle grip and are not affected by the movement of the slide, the slide block, the adjusting knob or the pull wire. The handle of the steerable catheter is useful for medical procedures where the catheter tip must be positioned and oriented precisely and where the control handle must be held in a precise position for an extended period of time.

DETAILED DESCRIPTION OF THE PREFERRED EMBODIMENT

The steerable catheter of the instant invention is comprised of two major portions. The first is the elongated catheter body (12) which is secured to, and the movement of which, is controlled by the second portion, the steerable catheter handle (14). The elongated catheter body (12) comprises a catheter body having a proximal end secured to the steerable catheter handle (14) and a distal end which incorporates a catheter tip. The catheter body is of elongated, tubular construction having one or more lumen. The catheter body is flexible, i.e., bendable, but substantially non-compressible along its length. The catheter body may be constructed of conventional material. A presently preferred construction comprises a nylon tube with a polymer coating containing a number of electrical electrode wires and a pull wire. The length and diameter of the catheter body are not generally critical but will vary according to the medical application.

The catheter tip comprises a short section of flexible tubing having one or more lumen. This flexible tubing may be made of any suitable material and preferably is more flexible than the catheter body. The catheter tip may be a separate component which is independently secured to the catheter body or formed as an integral part of the catheter body.

The diameter of the catheter tip is not critical but is preferably about the same as, or slightly smaller, than the diameter of the catheter body. The length of the catheter tip likewise is not critical. Its length may be influenced by the number of sensing elements present in the catheter tip. These sensing elements are generally electrodes formed in metal rings around the outer diameter of the catheter tip. In addition, conventionally a rounded tip electrode is positioned at the distal end of the catheter tip.

In steerable catheters a pull wire (18), preferably made of metal, extends from the steerable catheter handle (14) through a lumen of the catheter body and into a lumen located in the catheter tip. The pull wire (18) is then fixedly attached to the catheter tip electrode. The pull wire is preferably surrounded by a fluorotype polymer sheath or the like for lubricity to keep the pull wire generally co-axial within the catheter body. The means for attaching the pull wire to the tip electrode is conventional and can be accomplished by any of the known procedures in the industry such as fitting the distal end of the pull wire to the catheter tip electrode and crimping it securely or welding it in place.

Electrical electrode wires (16) extend through the steerable catheter handle (14) through one or more of the lumen of the catheter body and into one or more of the lumen of the catheter tip. The electrical electrode wires are then attached to the electrodes which are secured at the end or near the end of the catheter tip.

Figure 1:
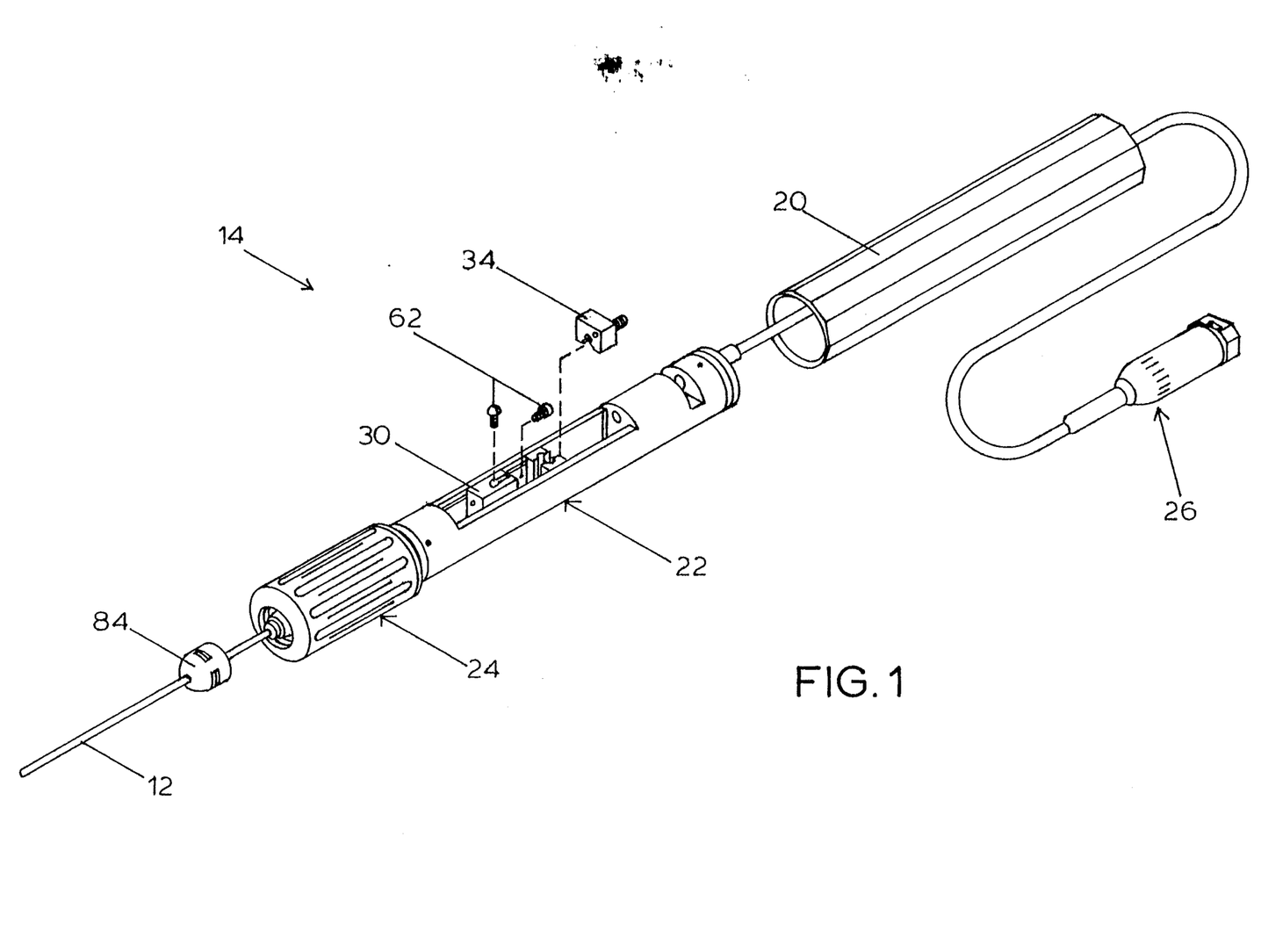
FIG. 1 is an exploded view of the control handle.

The steerable catheter handle (14), which is secured to the proximal end of the catheter body, is comprised of a handle grip (20), surrounding a mounting shaft (22) containing a number of components, secured at the distal end (38) of the mounting shaft is an adjustment knob (24) and secured at the proximal end (40) of the mounting shaft is an electrical connector (26). See FIG. 1.

The handle grip (20) surrounds the inner components of the steerable catheter handle. For ease of holding the handle grip is preferably multi-sided. In one preferred embodiment it is ten sided, although various other shapes and numbers of sides may be used as is considered appropriate. The handle grip is a hollow sheath open at both ends, fitting over the mounting shaft and can be produced from hard plastic or other suitable material, the composition of which is not critical.

Figure 2:
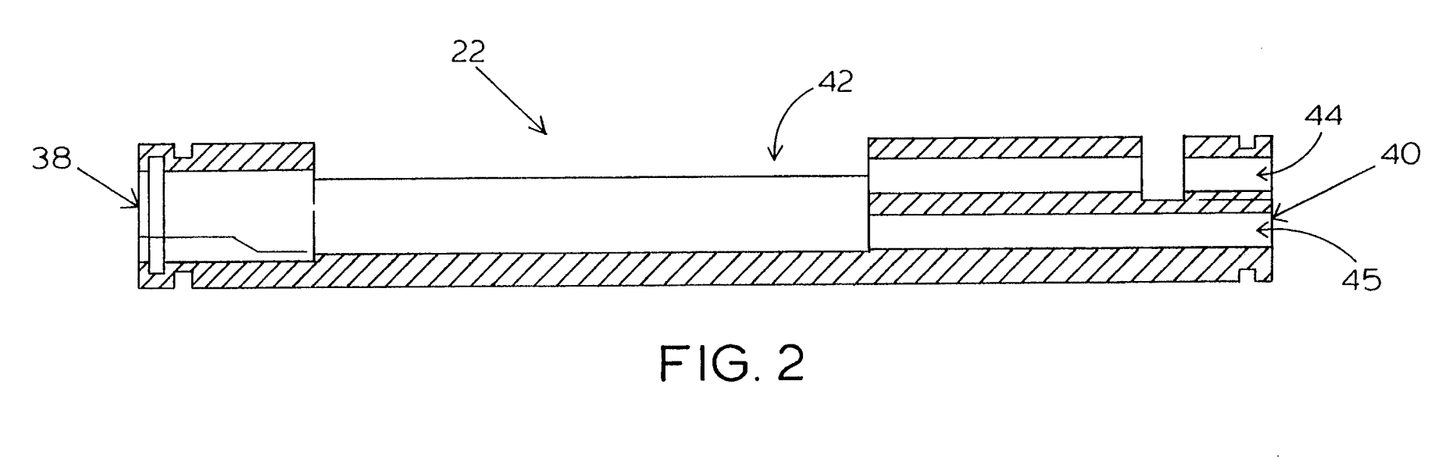
FIG. 2 is a side view of the mounting shaft.

The mounting shaft (22) is also prepared from a hard plastic or similar material and is generally tubular in construction. It contains a geared slide (28), a slide block (30) to secure the pull wire (18) in a fixed location, a slide block adjustment screw (32) for adjusting the location of the slide block (30), a spacer block (34) and an adjustment screw guide (36). The mounting shaft (22) is open at its distal end (38), has a cut away section (42) running approximately half the length of the mounting shaft and openings, preferably a pair of openings (44, 45), in the proximal end (40) of the mounting shaft. See FIG. 2.

Figure 3:
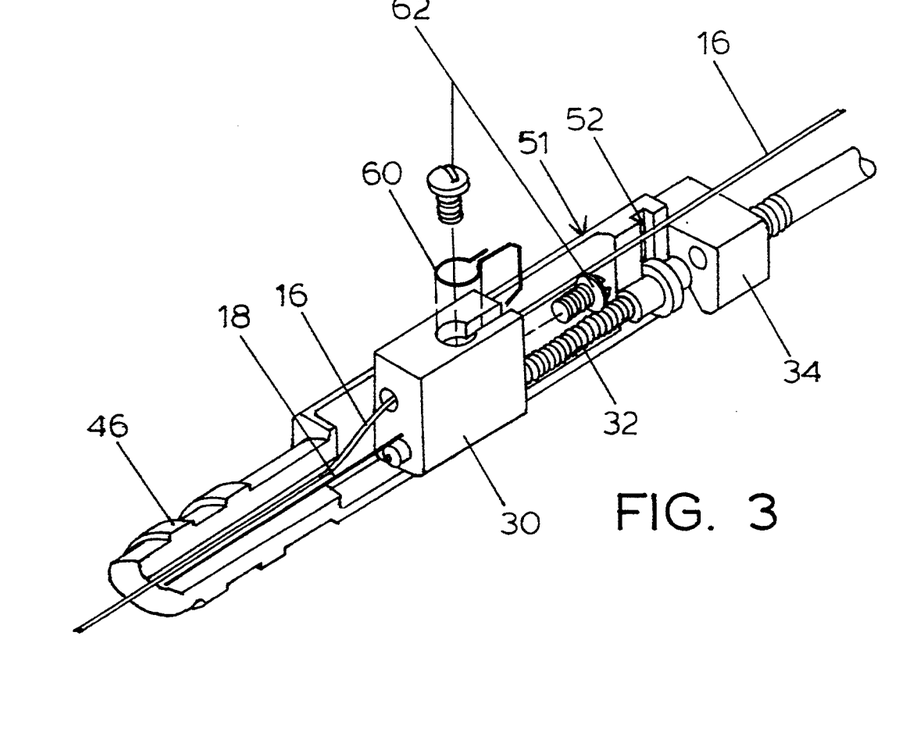
FIG. 3 is a side cut away view of the components inside the mounting shaft.
Figure 4:
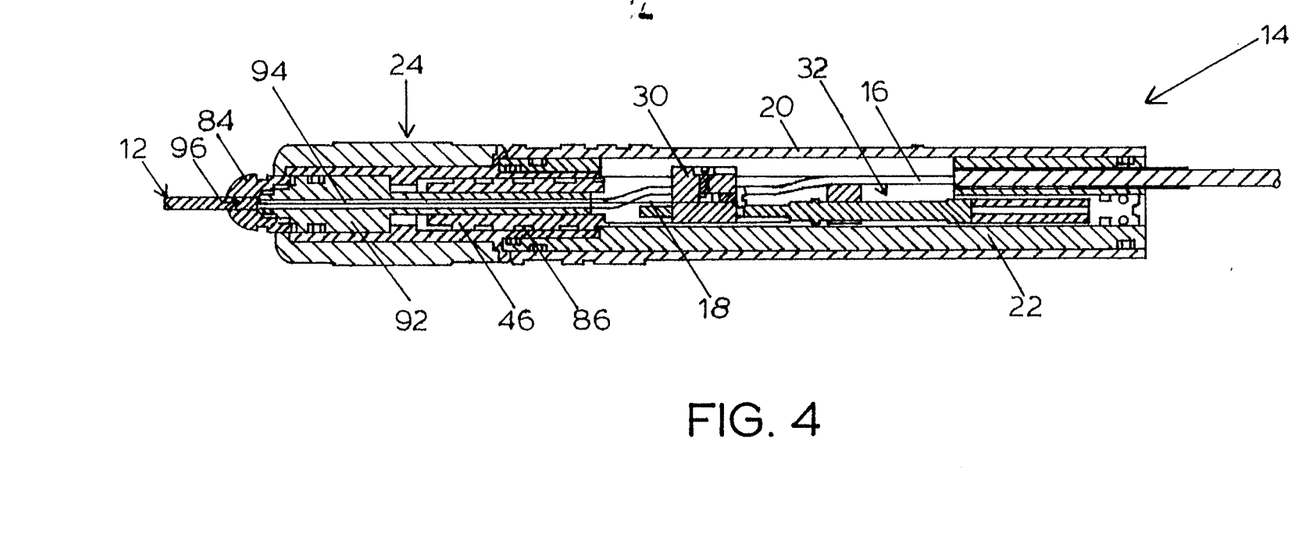
FIG. 4 is a side, cut away view of the control handle.
Figure 5:
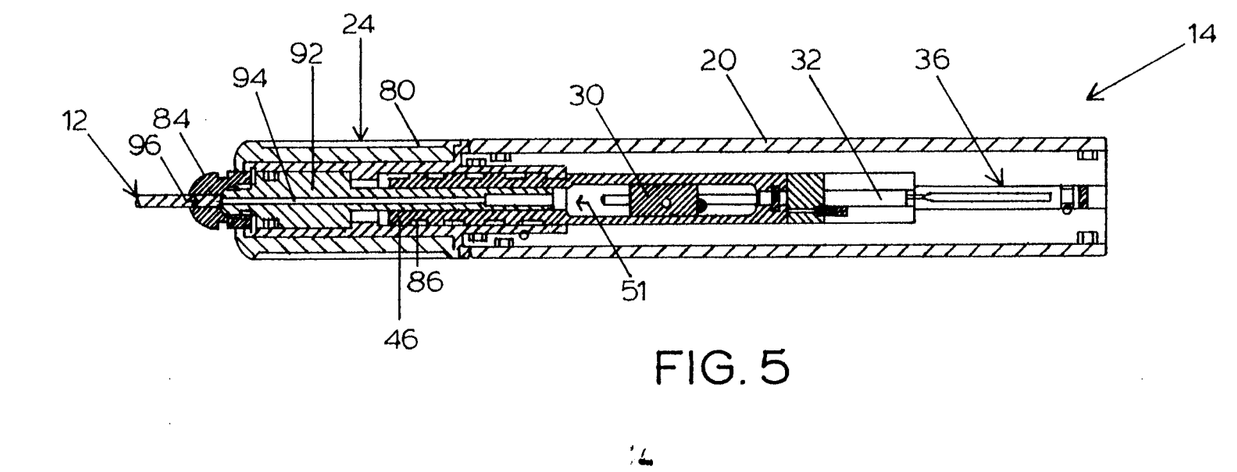
FIG. 5 is a top, cut away view of the control handle.
Figure 6:
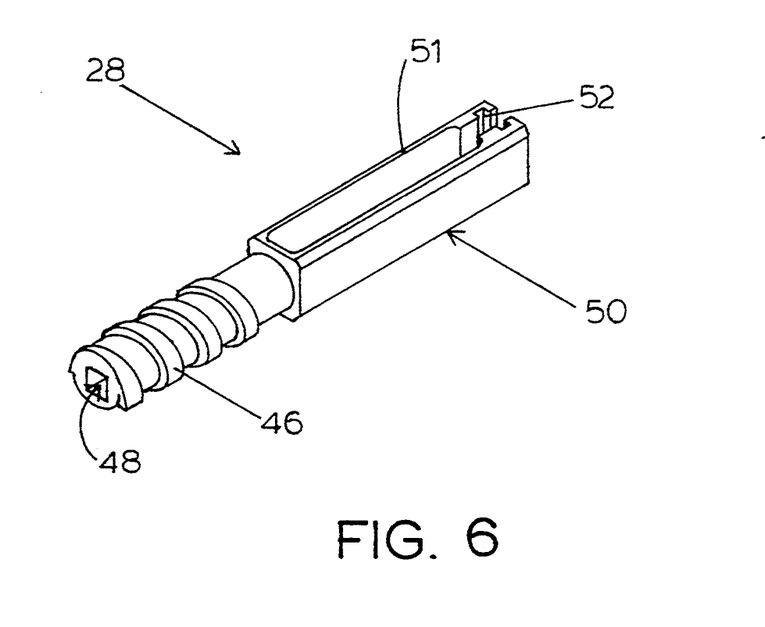
FIG. 6 is a perspective view of the geared slide of the control handle.

The geared slide (28) (see FIG. 6) fits generally within the cut away section (42) of the mounting shaft and is comprised of two sections. See FIGS. 3–5. The distal threaded section (46) is a circular, externally threaded section, containing an opening (48) in its distal end, preferably square in cross-section. The distal section of the geared slide is a worm gear which works in combination with the adjustment knob (24) to move proximally to distally within the mounting shaft (22). When fully extended, the distal threaded section (46) of the geared slide (28) extends beyond the distal end (38) of the mounting shaft (22) to interact with the adjustment knob (24). The proximal section (50) of the geared slide is generally square in cross-section, one side of which is open to form a box-like structure (51). See FIG. 6. Located at the proximal end of this box-like structure is a slot (52). See FIGS. 3 and 6.

Figure 8:
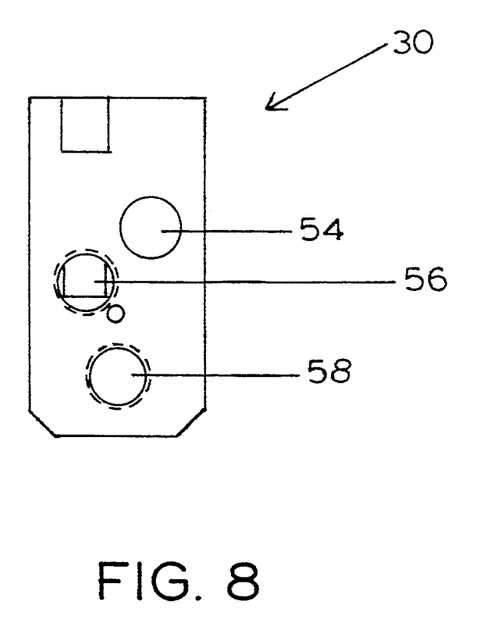
FIG. 8 is an end view of the slide block.

Within the box-like structure (51) of the geared slide (28) is placed the slide block (30). See FIG. 3. The slide block is an elongated rectangular piece taller than it is wide. The slide block has three tubular openings (54, 56, 58) which run through the block distally to proximally. See FIG. 8. The upper opening (54) provides a passageway for the electrode electrical wires. This opening is of sufficient size to permit the electrode electrical wires to pass freely through this opening as the slide block (30) moves within the geared slide (28). The middle opening (56) provides a passageway for the pull wire (18) which passes distally to proximally through this opening. After the pull wire passes through the proximal end of this opening, it is bent upward and on top of the slide block. The proximal tip (60) of the pull wire is then formed into a loop and placed within an opening in the top portion of the slide block and securely held in place by screws (62), one at the top and a second on the proximal end of the slide block. See FIG. 3. Other methods of attachment of the pull wire (18) to the slide block (30) can be used. The third opening (58) in the slide block is a geared opening through which the slide block adjustment screw (32) passes.

Figure 7:
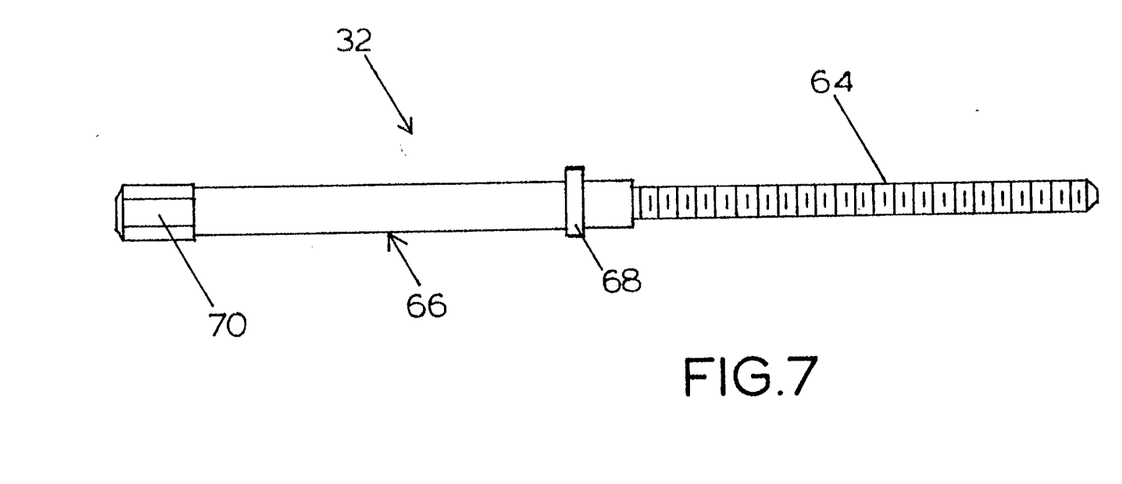
FIG. 7 is a side view of the slide block adjustment screw.

The slide block adjustment screw (32) is divided into four sections. See FIG. 7. Approximately one-half of the length of the slide block adjustment screw is a geared portion (64) which passes through the bottom most opening (58) in the slide block (30). See FIG. 3. As the slide block adjustment screw (32) is turned, the slide block is moved within the geared slide (28) proximally or distally. A significant portion of the remaining slide block adjustment screw is circular in cross-section and located near the proximal end of the slide block adjustment screw. Located on this circular section (66) of the slide block adjustment screw is a ring section (68). This ring section (68) extends out from the surface of the circular section (66) of the slide block adjustment screw and fits within the slot (52) of the geared slide (28). See FIG. 3. Thus, as the geared slide (28) moves distally within the mounting shaft (22), the slot (52) in the geared slide pushes the ring portion (68) distally, thus pushing the slide block adjustment screw (32) forward. The proximal end of the slide block adjustment screw (32) contains a hexagonal end section (70) which is slightly larger in diameter than the circular portion (66) of the slide block adjustment screw.

Located proximally from the ring section (68) of the slide block adjustment screw and placed against the proximal end of the box-like structure (51) of the geared slide (28) is the spacer block (34). See FIGS. 3, 4, 5 and 8. The thickness of this spacer block can be adjusted as needed by the manufacturer. The purpose of the spacer block is to limit the extent of the proximal movement of the geared slide (28). As the geared slide moves proximally within the mounting shaft (22), the spacer block (34) which is placed over the circular section (66) of the slide block adjustment screw moves proximally with the geared slide (28) until the proximal end of the spacer block meets the proximal end of the cut away section (42) of the mounting shaft, thus preventing further proximal movement of the geared slide (28). The larger the movement of the geared slide (28) within the mounting shaft (22), the greater the bending of the catheter tip. Thus, by increasing and decreasing the thickness of the spacer block (34), the extent of deflection of the catheter tip can be controlled.

Figure 9:
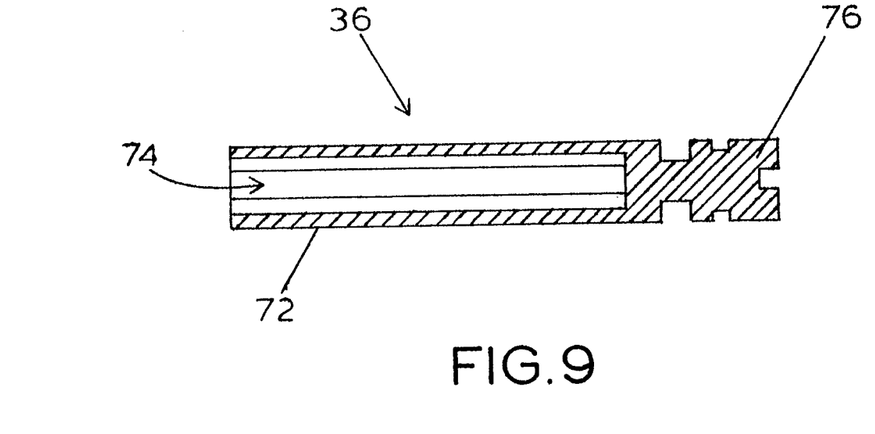
FIG. 9 is a top view of the adjustment screw guide.

Proximal from the slide block adjustment screw (32) is the adjustment screw guide (36). See FIG. 9. The slide block adjustment screw guide (36) is divided into two main sections, a distal tube section (72), whose internal opening (74) is hexagonally shaped, and a proximal screw head section (76). The hexagonal end section (70) of the slide block adjustment screw (32) fits within the distal, hexagonally shaped tube section (72) of the adjustment screw guide (36). The tube section (72) of the adjustment screw guide is generally circular in cross-section extending approximately two-thirds of the way from the distal tip of the adjustment screw guide. This hexagonally shaped internal opening (74) is designed to function in combination with the proximal hexagonal end section (70) of the slide block adjustment screw (32).

The proximal end of the mounting shaft has two openings (44, 45). The upper opening (44) is a passageway for the sheathed electrode electrical wires which ultimately connect to an electrical connector at the proximal end of the device. The lower opening (45) is an opening for the proximal end of the slide block adjustment screw guide. The proximal screw head section (76) of the adjustment screw guide (36) extends through this lower opening (45) in the proximal end of the mounting shaft. By rotation of this screw head section (76), the adjustment screw guide (36) will rotate either clockwise or counterclockwise. As the adjustment screw guide (36) is rotated, it will also rotate the hexagonal end section (70) of the slide block adjustment screw (32) which passes through the slide block (30). As both the distal portion of the slide block adjustment screw and the bottom opening (58) in the slide block are threaded, the slide block (30) can be moved axially, either distally or proximally, as desired. This feature permits fine adjustments to the location of the slide block (30) and the associated pull wire (18) within the steerable catheter handle (14). Various O-rings and other conventional components may be connected to the adjustment screw guide and to the other components of the steerable catheter handle (14) to permit rotation of those components as needed.

Figure 10:
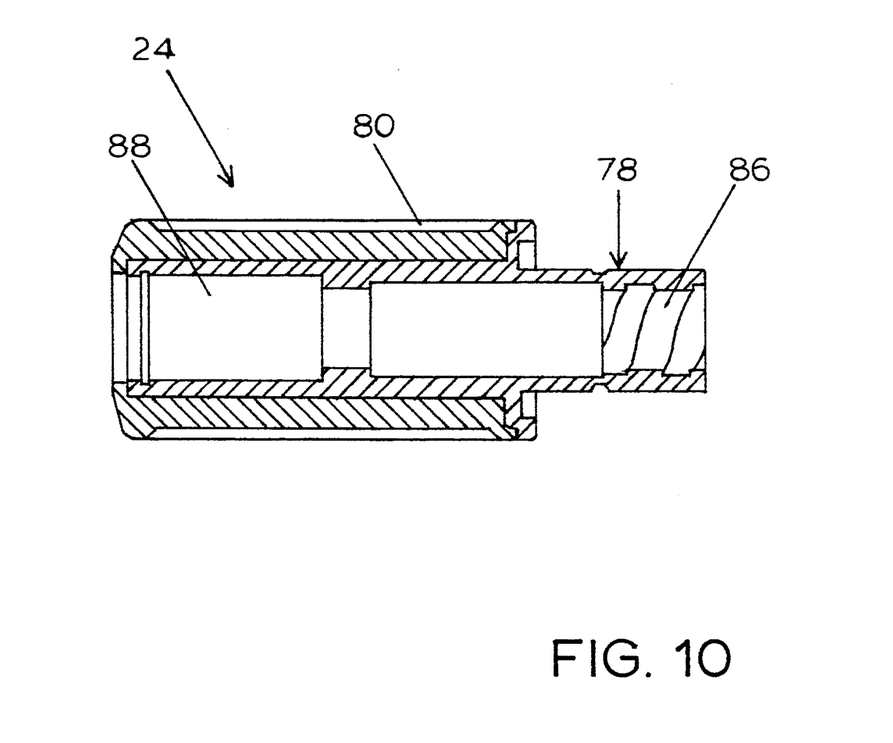
FIG. 10 is a side cut away view of the adjusting knob.
Figure 11:
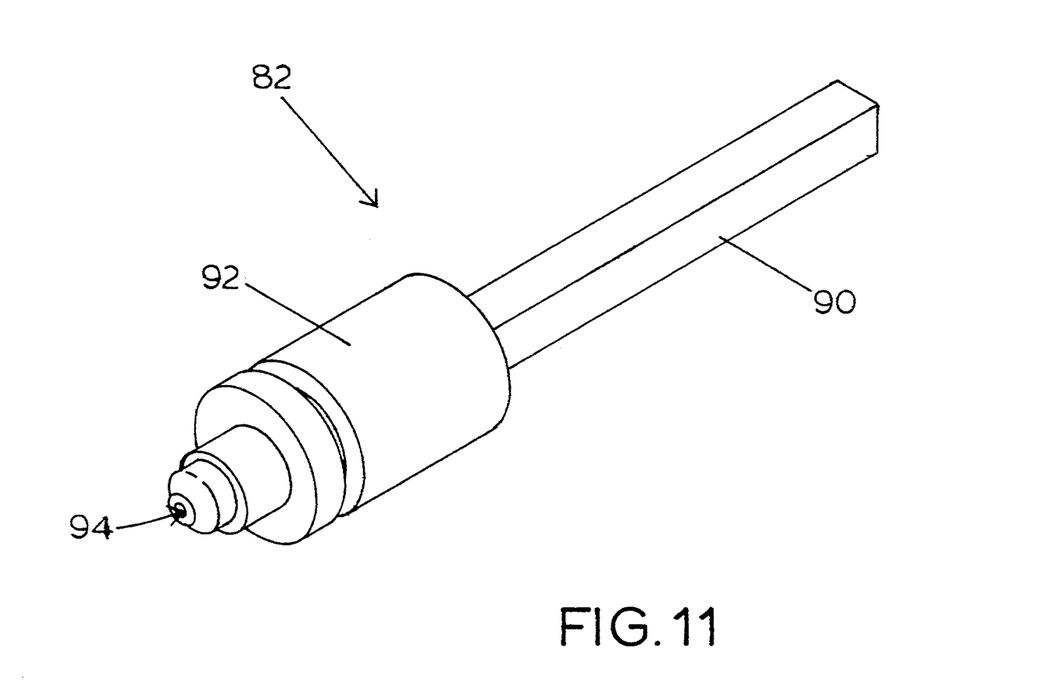
FIG. 11 is a perspective view of the wire guide.

Distally from the mounting shaft is the adjustment knob (24). See FIGS. 1 and 10. The adjustment knob is comprised of a geared insert (78) in the adjustment knob, an external rotation element (80), a wire guide (82) (See FIG. 11) and a catheter retaining nut (84). See FIG. 1. Rotation of the adjustment knob (24) advances or withdraws the geared slide (28) of the mounting shaft. By this movement the pull wire is put under tension or relieved from tension.

The critical component of the adjustment knob is the geared insert (78). The geared insert is secured within the external rotation element (80) by securely placing it within such element with close tolerances. It may be held in place by conventional means. The geared insert (78) is a hollowed out tube divided into two sections. See FIG. 10. The proximal section (86) of the geared insert is internally geared through which the threaded section (46) of the geared slide (28) moves. The distal section is a rounded tube section (88) which holds the wire guide (82) in place.

The wire guide (82) guides both the pull wire (18) and the electrical electrode wires (16) from the steerable catheter handle (14) to the catheter body (12). See FIG. 11. The wire guide is divided into two sections, a square cross-sectioned portion (90) and a rounded section (92). The square cross-sectioned portion (90) operates within the square cross-sectioned opening (48) within the distal tip of the geared slide (28). See FIGS. 4, 5 and 6. This permits the distal end of the geared slide (28) to move over the square cross-sectioned portion (90) of the wire guide (82) without allowing axial rotation. The rounded section (92) of the wire guide fits within the geared insert (78). However, as the geared insert (78) is rotated, the rounded section (92) is prevented from rotation by the interaction of the square cross-sectioned portion (90) of the wire guide (82) and the squared opening (48) in the geared slide (28). As the pull wire (18) and the electrical electrode wires (16) pass through a lumen (94) in the wire guide, they are joined to form part of the catheter body. See FIG. 4. Appropriate o-rings and lubrication are provided to permit easy rotation, reducing the friction between the components of the adjustment knob.

The distal tip of the steerable catheter handle contains the catheter retaining nut (84). See FIG. 1. The catheter retaining nut is joined to the distal tip of the wire guide (82). As the catheter body passes through a lumen (96) in the catheter retaining nut, the catheter body is slightly enlarged in cross-section to engage the lumen (96) of the catheter retaining nut. This engagement constricts the movement of the catheter body as the external rotation element (80) of the adjustment knob (24) is rotated.

The outermost portion of the adjustment knob (24) is the external rotation element (80) whose function is to rotate the geared insert (78). See FIG. 10. This external rotation element (80) can be constructed of any material that will provide good feel to the user of the product, such as a soft, flexible rubber-type material. Preferably, it contains ridges and/or slots running proximally to distally to provide fine control of the rotation of the external rotation element.

In operation, the catheter tip is inserted into a vein, artery or other body lumen which is located near the body surface. The catheter body (12) is then guided to the appropriate location in the human body for the selected medical procedure. To assist in this movement, the tip of the catheter body can be bent by operation of the steerable catheter handle (14). The controlled bending of the catheter tip permits precise control of the movement of the catheter body. To put the pull wire (18) in tension which bends the catheter tip, the external rotation element (80) of the adjustment knob (24) is rotated clockwise, as viewed from proximal end of catheter handle. As it is rotated, the geared insert (78) within the adjustment knob (24) interacts with the geared slide (28) in the mounting shaft (22) to put the pull wire (18) in tension, thus bending the catheter tip. To remove the bend from the catheter tip, the adjustment knob (24) is rotated in the opposite direction, thus removing the tension from the pull wire (18). To provide precise control of the pull wire within the steerable catheter handle and to limit the amount of deflection, the adjustment screw guide (36) can be adjusted by rotating the screw head portion (76) at the proximal end (40) of the mounting shaft (22). By clockwise and counterclockwise movement of the adjustment knob (24), precise bending of the catheter tip can be achieved. The catheter tip may also be rotated axially by rotation of the entire catheter handle. Precise movement of the catheter tip can be attained by the use of only one hand of the medical personnel, freeing the other hand for other activities relating to the medical procedure being performed.

We claim:

1. A steerable catheter comprising
   (a) a flexible elongated catheter body containing one or more lumens, having proximal and distal ends,
   (b) a flexible catheter tip fixedly secured to the distal end of the catheter body,
   (c) an elongated pull wire running through the catheter body having its distal end secured to the catheter tip, and
   (d) a steerable catheter handle secured to the proximal end of the catheter body wherein said catheter handle is comprised of a mounting shaft containing securing means for securing the proximal end of the pull wire, tensioning means for putting the pull wire in tension and relieving the tension on the pull wire within the catheter body, an adjustment knob containing an internally geared portion which operates in conjunction with the tensioning means to put the pull wire in tension and relieve the tension on the pull wire, a handle grip secured to the mounting shaft and an electrical connector connected to the proximal end of the mounting shaft.

2. The steerable catheter of claim 1 wherein the mounting shaft incorporates a geared slide, a slide block to secure the pull wire in place, and a slide block adjustment screw threaded through the slide block.

3. The steerable catheter of claim 2 wherein a spacer block is secured to the slide block adjustment screw.

4. The steerable catheter of claim 2 wherein an adjustment screw guide is incorporated within the mounting shaft to operate in conjunction with the slide block adjustment screw.

5. The steerable catheter of claim 4 wherein the slide block adjustment screw is divided into four sections comprising a geared section, a non-geared circular section, a ring section and a tip section secured to the proximal end of the circular section.

6. The steerable catheter of claim 5 wherein the tip of the slide block adjustment screw interacts with an opening in the distal end of the adjustment screw guide.

7. The steerable catheter of claim 2 wherein the adjustment knob includes an external rotation element, a geared insert, a wire guide and a catheter retaining nut.

8. The steerable catheter of claim 7 wherein the proximal end of the wire guide has a square cross-section to interact with a square opening in the distal tip of the geared slide of the mounting shaft.

9. The steerable catheter of claim 7 wherein the catheter retaining nut is secured to the distal end of the wire guide such that upon rotation of the external rotation element of the adjustment knob, the catheter retaining nut will not rotate.

10. The steerable catheter of claim 9 wherein the catheter body is prevented from axial rotation by the catheter retaining nut.

11. The steerable catheter of claim 1 wherein the securing means is a slide block which has three openings passing there through, the first for the pull wire, the second for electrode electrical wires contained within the catheter body and the third of which is threaded.

12. The steerable catheter of claim 4 wherein the proximal end of the adjustment screw guide has a screw head opening such that it may be rotated while in place in the mounting shaft.

13. The steerable catheter of claim 12 wherein upon rotation of the adjustment screw guide, the distal end of the adjustment screw guide interacts with a hexagonal proximal tip of the slide block adjustment screw to rotate the slide block adjustment screw.

14. The steerable catheter of claim 11 wherein the proximal end of the pull wire is held in place against the slide block.

15. The steerable catheter of claim 1 wherein the handle grip has ten sides, is open at both the proximal and distal end and fits over the mounting shaft.

16. The steerable catheter of claim 1 wherein the tensioning means is a combination of a geared slide and a slide block wherein the proximal end of the pull wire is secured to the slide block.

17. A steerable catheter comprising
   (a) a flexible elongated catheter body containing one or more lumens, having proximal and distal ends,
   (b) a flexible catheter tip fixedly secured to the distal end of the catheter body,
   (c) an elongated pull wire running through the catheter body having its distal end secured to the catheter tip, and
   (d) a steerable catheter handle secured to the proximal end of the catheter body wherein said catheter handle is comprised of a mounting shaft wherein the mounting shaft incorporates a geared slide, a slide block to secure the pull wire in place, and a slide block adjustment screw threaded through the slide block tensioning means for putting the pull wire in tension and relieving the tension on the pull wire within the catheter body, an adjustment knob containing an internally geared portion which operates in conjunction with the tensioning means to put the pull wire in tension and relieve the tension on the pull wire, a handle grip secured to the mounting shaft and an electrical connector connected to the proximal end of the mounting shaft.

18. The steerable catheter of claim 17 wherein a spacer block is secured to the slide block adjustment screw.

19. The steerable catheter of claim 17 wherein an adjustment screw guide is incorporated within the mounting shaft to operate in conjunction with the slide block adjustment screw.

20. The steerable catheter of claim 19 wherein the slide block adjustment screw is divided into four sections comprising a geared section, a non-geared circular section, a ring section and a tip section secured to the proximal end of the circular section.

21. The steerable catheter of claim 20 wherein the tip of the slide block adjustment screw interacts with an opening in the distal end of the adjustment screw guide.

22. The steerable catheter of claim 17 wherein the adjustment knob includes an external rotation element, a geared insert, a wire guide and a catheter retaining nut.

23. The steerable catheter of claim 22 wherein the proximal end of the wire guide has a square cross-section to interact with a square opening in the distal tip of the geared slide of the mounting shaft.

24. The steerable catheter of claim 22 wherein the catheter retaining nut is secured to the distal end of the wire guide such that upon rotation of the external rotation element of the adjustment knob, the catheter retaining nut will not rotate.

25. The steerable catheter of claim 24 wherein the catheter body is prevented from axial rotation by the catheter retaining nut.

26. The steerable catheter of claim 19 wherein the proximal end of the adjustment screw guide has a screw head opening such that it may be rotated while in place in the mounting shaft.

27. The steerable catheter of claim 26 wherein upon rotation of the adjustment screw guide, the distal end of the adjustment screw guide interacts with a hexagonal proximal tip of the slide block adjustment screw to rotate the slide block adjustment screw.

28. A steerable catheter comprising
   (a) a flexible elongated catheter body containing one or more lumens, having proximal and distal ends,
   (b) a flexible catheter tip fixedly secured to the distal end of the catheter body,
   (c) an elongated pull wire running through the catheter body having its distal end secured to the catheter tip, and
   (d) a steerable catheter handle secured to the proximal end of the catheter body wherein said catheter handle is comprised of a mounting shaft containing securing means for securing the proximal end of the pull wire, wherein the securing means is a slide block which has three openings passing there through, the first for the pull wire, the second for electrode electrical wires contained within the catheter body and the third of which is threaded, tensioning means for putting the pull wire in tension and relieving the tension on the pull wire within the catheter body, an adjustment knob containing an internally geared portion which operates in conjunction with the tensioning means to put the pull wire in tension and relieve the tension on the pull wire, a handle grip secured to the mounting shaft and an electrical connector connected to the proximal end of the mounting shaft.

29. The steerable catheter of claim 28 wherein the proximal end of the pull wire is held in place against the slide block.

30. A steerable catheter comprising
   (a) a flexible elongated catheter body containing one or more lumens, having proximal and distal ends,
   (b) a flexible catheter tip fixedly secured to the distal end of the catheter body,
   (c) an elongated pull wire running through the catheter body having its distal end secured to the catheter tip, and
   (d) a steerable catheter handle secured to the proximal end of the catheter body wherein said catheter handle is comprised of a mounting shaft containing securing means for securing the proximal end of the pull wire and tensioning means for putting the pull wire in tension and relieving the tension on the pull wire within the catheter body, wherein the tensioning means is a combination of a geared slide and a slide block, wherein the proximal end of the pull wire is secured to the slide block, an adjustment knob containing an internally geared portion which operates in conjunction with the tensioning means to put the pull wire in tension and relieve the tension on the pull wire, a handle grip secured to the mounting shaft and an electrical connector connected to the proximal end of the mounting shaft.

31. The steerable catheter of claim 30 wherein the handle grip has ten sides, is open at both the proximal and distal end and fits over the mounting shaft.

* * * * *